(12) United States Patent
Sen et al.

(10) Patent No.: US 6,383,138 B1
(45) Date of Patent: May 7, 2002

(54) METHOD FOR TRANSDERMAL SAMPLING OF ANALYTES

(75) Inventors: Arindam Sen; Sek Wen Hui, both of Williamsville; Ya Li Zhao, Amherst, all of NY (US)

(73) Assignee: Health Research, Inc., Buffalo, NY (US)

( * ) Notice: Subject to any disclaimer, the term of this patent is extended or adjusted under 35 U.S.C. 154(b) by 0 days.

(21) Appl. No.: 09/793,257

(22) Filed: Feb. 26, 2001

Related U.S. Application Data (60) Provisional application No. 60/184,919, filed on Feb. 25, 2000.

(51) Int. Cl.[7] .............................. A61B 5/00; A61N 1/30
(52) U.S. Cl. .......................... 600/365; 604/20; 600/573
(58) Field of Search ................................. 600/345, 347, 600/365, 372, 573, 584; 435/14; 204/403; 604/20–22, 289, 290

(56) References Cited

U.S. PATENT DOCUMENTS

| | | | |
|---|---|---|---|
| 4,953,552 A | 9/1990 | DeMarzo | 128/635 |
| 5,983,131 A | 11/1999 | Weaver et al. | 604/20 |
| 6,041,252 A | * 3/2000 | Walker et al. | 604/20 |
| 6,048,545 A | * 4/2000 | Keller et al. | 424/450 |
| 6,144,869 A | 11/2000 | Berner et al. | 600/347 |
| 6,148,232 A | * 11/2000 | Avrahami | 604/20 |
| 6,207,400 B1 | 3/2001 | Kwon | 435/14 |
| 6,251,433 B1 | * 6/2001 | Zuckermann et al. | 424/486 |

OTHER PUBLICATIONS

Hui, Effects of Pulse Length and Strength on Electroporation Efficiency, 1995, In: Methods in Molecular Biology, vol. 48: Animal Cell Electroporation and Electrofusion Protocols, pp. 29–40.
Powell et al., Tissue Electroporation—Observation of Reversible Electrical Breakdown in Viable Frog Skin, 1989, Biophysical Journal, vol. 56, pp. 1163–1171.
Prausnitz et al., Electroporation of Mammalian Skin: A Mechanism to Enhance Transdermal Drug Delivery, Nov. 1993, Proc. Nat. Acad. Sci., USA, vol. 90, pp. 10504–10508.
Mezei, Liposomes in the Topical Application of Drugs: A Review, 1988, In: Liposomes as Drug Carriers, pp. 663–677.
Li et al., Product–Delivering Liposomes Specifically Target Hair Follicles in Histocultured Intact Skin, Nov.–Dec. 1992, In Vitro Cell Dev. Biol., 28A:679–681.
Li et al., Liposome Targeting of High Molecular Weight DNA to the Hair Follicles of Histocultured Skin: A Model for Gene Therapy of the Hair Growth Processes, Apr. 1993, In Vitro Cell Dev. Biol., 29A:258–260.

* cited by examiner

Primary Examiner—Kevin Shaver
Assistant Examiner—Charles Marmor, II
(74) Attorney, Agent, or Firm—Hodgson Russ LLP (57) ABSTRACT

The present invention discloses a method for transdermal extraction and measurement of analytes in an individual's body comprising the steps of permeabilizing the skin by electroporation in the presence of liposomes comprising negatively charged lipids, and extracting the extracellular fluid through the permeabilized skin by using suction. Analytes may be quantitated in the extracted extracellular fluid.

22 Claims, 6 Drawing Sheets

METHOD FOR TRANSDERMAL SAMPLING OF ANALYTES

This application claims priority of U.S. provisional application serial No. 60/184,919 filed on Feb. 25, 2000, the disclosure of which is incorporated herein by reference.

FIELD OF INVENTION

The present invention relates generally to the field of transdermal extraction and sampling of analytes. More particularly, the present invention provides a method for extraction and sampling of analytes by electroporation in the presence of liposomes.

DISCUSSION OF RELATED ART

The ability to accurately measure analytes such as glucose in the blood is important for management of disease. For example, proper monitoring of blood glucose levels prior to or following insulin injections could result in easier management of diabetes.

Conventional monitoring of blood analytes requires drawing of a blood sample. However, pain and inconvenience associated with frequent drawing of blood may cause patients to miss monitoring routines. To overcome problems associated with invasive techniques, several approaches have been proposed that involve extraction of analytes through skin.

Mammalian skin has two layers, the epidermis and the dermis. The epidermis is a stratified squamous keratinizing epithelium. The uppermost stratum of the epidermis is the stratum corneum (SC) which consists of about 20 layers of flattened, enucleate, keratin-filled corneocytes surrounded by lamellae of about 8 lipid bilayers on average. The bilayers consist primarily of cholesterol, free fatty acids and ceramide. The total thickness of the SC varies from 10 to 40 $\mu$m, with an average thickness of 20 $\mu$m (Chizmadzhev et al., 1995, *Biophysical Journal*, 68:749–765; Bouwstra et al., 1995; *Pharmaceutical Research* 11 (12):1809–1814; Swartzendruber et al., 1989, *Journal of Investigative Dermatology*, 92:251–257). The SC layer constitutes the major electric resistance of the skin (Rosendahl, 1945, *Acta Physiol. Scan.* 9:39), and is the main barrier to substance transport. Thus, transdermal extraction approaches have typically involved techniques which increase permeability of the SC layer. Examples of such techniques are iontophoresis, ultrasound, and vacuum.

Iontophoresis requires the use of electrodes containing oxidation-reduction species as well as passing electric current through the skin. A DC field is used to transport molecules through the SC via appendageal or paracellular space. However, the non-permeable nature of SC and the side effects associated with iontophoresis such as irreversible skin damage, limit the use of iontophoresis for transdermal sampling.

Vacuum has been used to draw fluid transdermally for sampling (U.S. Pat. No. 6,009,343). However,.the impermeability of the stratum corneum layer limits the use of this technique.

Ultrasound is believed to disrupt the lipid layers between the keratinocytes in the stratum corneum and thereby improve permeability of the skin. Methods involving ultrasound are disclosed in U.S. Pat. Nos. 4,767,402; 4,780,212 and 5,115,805.

Another method to transiently permeabilize skin is by the application of a single or multiple short duration pulses. The predominant voltage gradient across the skin develops across the non-conductive SC. If the voltage gradient exceeds the barrier breakdown potential, pores are formed which reseal depending on the applied pulse field and duration (Hui, 1995, *In: Methods in Molecular Biology*, Vol:48 *Animal cell Electroporation and Electrofusion Protocols*, J. A. Nickoloff, ed. Humana Press, pp. 29–40). During the lifetime of the pores, materials may be transported across the barrier (Powell et al., 1989, *Biophysical Journal* 56:1163–1171; Prausnitz et al.,1993, *Proc. Nat. Acad. Sci., USA* 90:10504–10508). While electroporation has been used for delivery of materials, it has not been used heretofore for the extraction and sampling of body analytes such as glucose.

Although liposomes have been used for topical transdermal drug administration with various degrees of effectiveness, the mechanism is still debatable (Mezei, 1988, *In: Liposomes as drug carriers*, Gregoriadis G. Ed.,Wiley, New York). When applied to the histocultured murine skin surface, neutral liposomes were reported to concentrate in the hair follicle channels (Li et al., 1992, *In Vitro Cell Dev. Biol.* 28A:679–681; Li et al., 1993, *In Vitro Cell Dev. Biol.* 29A:258–260). Based on the above, the role of liposomes in analyte extraction and sampling is not clear. Moreover, no quick and efficient techniques exist for extraction and analysis of blood analytes. Consequently, there is an ongoing need to develop new approaches for extraction and sampling of analytes so as to allow easy monitoring and management of diseased states.

SUMMARY OF THE INVENTION

The present invention provides a method for transdermal sampling of analytes. The method comprises forming a local area of permeabilized skin by contacting the skin with liposomes comprising negatively charged lipids, and passing an electric pulse through the permeabilized skin. Extracellular fluid is then collected by application of suction in the permeabilized area. The collected fluid can then be used for detecting the presence of desired analytes.

The negatively charged lipids may be mixed with other negatively charged or uncharged lipids to form liposomal compositions useful for the present invention. Thus, in a preferred embodiment, liposomes were formed by negatively charged phospholipid dioleylphosphatidylglycerol (DOPG) with and without uncharged dioleylphosphatidyl choline (DOPC).

BRIEF DESCRIPTION OF THE DRAWINGS

FIG. 4 is a representation of the recovery of electrical resistance of mouse skin following the application of 1(◆), 2(■), 60 (●) and 180 (▲) pulses of 100V, 1 msec duration.

Liposomes were added to the compartment facing the outer surface of the skin.

DETAILED DESCRIPTION OF THE INVENTION

The present invention provides a method for transdermal extraction and sampling of analytes. The method comprises the steps of permeabilizing an area of the skin by using a combination of liposomes and electroporation. Extracellular fluid is then suctioned through the permeabilized area and can be used for the detection and quantification of desired analytes.

While any analyte that can be extracted through the permeabilized skin may be quantitated, one analyte of particular clinical and therapeutic significance is glucose. Other analytes include, but are not limited to, electrolytes such as sodium, potassium and calcium; toxins; therapeutic and pharmacologic agents; drugs of abuse; amino acids; blood gases; lipids such as cholesterol; hormones such as insulin; enzymes, antibodies, cytokines and other biologically relevant molecules. Following extraction, detection and quantitation of the analyte may be carried out by any standard chemical,: physical, enzymatic and/or optical means.

The method of the present invention comprises applying one or more electric pulses and exposing the skin to liposomes to permeabilize it and then collecting extracellular fluid by applying suction. The liposomes useful for the present invention comprise negatively charged lipids. Suitable examples of such lipids include phosphatidylglycerol (including dioleylphosphatidylglycerol (DOPG)), phosphatidylserine, diphosphatidylglycerol (cardiolipin) and free fatty acids. The negatively charged lipids may be used alone or mixed with other negatively charged or neutral lipids. In one embodiment, the negatively charged lipid DOPG was mixed with uncharged dioleylphosphatidyl choline (DOPC) to form liposomes for the present invention.

The liposomes are contacted with an area of the skin. The skin may be shaved, if necessary, to provide for better electrical contact. Electrically conducting gels may also be applied to enhance electric contact. The liposomes may be contacted with the skin by adding to the electrode reservoir or may be contacted with the skin independent of the electrodes. A suitable example of an electrode containing a reservoir is a standard. skin electrode. A suitable skin electrode system is a silver/silver chloride system. Skin electrodes are available commercially such as from IVM Inc., Healdsburg, Calif. Electroporation is then carried out as follows. A negative electrode containing the liposomal composition in its reservoir, and a positive electrode are placed on a suitable area of the skin. Any standard pulse generator available commercially may be used to apply an electric potential between the electrodes. Preferably a potential drop of about 30V to about 180V, and more preferably about 80V to about 100V across each skin passage is suitable. The term "skin passage" as used herein means the area under the electrode through which current can pass between the electrode and the underlying tissue during the application of the electric pulses. The electric pulse may be a single one or multiple ones and the permeablization process may last from a fraction of a second to several minutes. The duration of the pulse is. preferably 1 msec, but may last from 10 μsec to 10 msec.

Those skilled in the art will recognize that liposomes need not be contacted with the skin at the same time as the application of the electric pulse. Liposomes may be first applied to the skin for a period of time and subsequently electric pulse may be applied to the same area.

In one embodiment of the invention, transdermal sampling and extraction of the specific molecule can be achieved by using electrode assemblies placed on exposed skin surface. The electrode assemblies can have a reservoir for the lipid formulation, the electrodes for application of electric pulse and a collector for the molecules extracted from the systemic fluids through the skin. Electric pulses can be applied to the set of electrodes using a bench-tip pulse generator or a small portable generator. The detection/ quantitation for measuring the amount of the extracted molecule can be performed either using a stand-alone unit or can be integrated together with the sampling electrode. assemblies. The detection system can be calibrated using standard techniques known to those skilled in the art.

Following application of an electric pulse in the presence of liposomes to permeabilize an area of the skin, suction is applied to the permeabilized area. The suction required to obtain the extracellular fluid after permeabilizatibn may be applied simply by a standard pipette connected to a collection chamber. A standard suction pump may also be used. A pressure of between about 50 mm and about 250 mm of Hg is sufficient for the fluid to be extracted. In one embodiment, the negative electrode can itself be connected to suction means. The suction may be provided by a small vacuum pump. An absorbent material can be placed in the reservoir of the negative electrode and suction applied. The absorbent material is removed from the reservoir and the presence of analyte is detected in the absorbent material. The raw data is calibrated against a set of standards to estimate the level of the analyte in the blood or tissue.

Any absorbent materials may be used for the present invention. Suitable materials include, but are not limited to, cotton, filter paper, absorbent gels and any material that can hold aqueous liquids may be used.

The present invention will be demonstrated by the following examples which are intended to be illustrative and are not to be construed as restrictive.

EXAMPLE 1

This embodiment illustrates the preparation of lipid formulations and liposomes used in the present invention. Any negatively charged lipid may be used to prepare liposomes. The negatively charged lipids may be mixed with other -negatively charged lipids or uncharged lipids. The lipid solutions in chloroform are mixed at the desired ratio. The solution is dried under nitrogen and placed under vacuum to remove any remaining solvent. The dried lipids may then be dispersed in a suitable buffer by vortexing. In one illustration of this embodiment, negatively charged. dioleylphosphtidylglycerol was mixed with uncharged dioleylphosphatidyl choline at an approximate 1:1 molar ratio and dispsersed in buffer by vigorous vortexing resulting in the formation of liposomes.

EXAMPLE 2

This embodiment illustrates that the analyte glucose can cross the stratum corneum using the method of the present invention. The stratum corneum layer was obtained by heat treatment of porcine skin-as-follows. Fresh pieces of porcine skin were wrapped in aluminum foil and placed in a 60° C. water. In about 5 minutes, the stratum corneum can be gently pulled away by hand from the rest of the skin tissue. The isolated SC layer was used in a Vertical Diffusion Chamber (such as commercially available from Crown Glass Co., Sommerville, N.J.). This simple device is well accepted as a model system for skin. The upper chamber was considered as the outer surface of the skin and the lower chamber as the skin directly below the stratum corneum. Platinum wires served as electrodes, one was placed in the upper chamber and the other in the lower chamber. Electric pulses were applied across the SC using a pulse generator The lipid formulation prepared as described in Example 1 was placed in the upper chamber (acceptor) and pulsed using negative pulses (375V, 1 msec pulse width, 1 Hz pulse repetition frequency) for 10 min. Glucose solution in buffer was then added to the lower chamber (donor). During the next 10 min no pulses were applied. An aliquot of the buffer was removed from the upper chamber. Pulses were next applied for 10, 20 and 30 min and aliquots removed from the upper chamber for analysis to determine movement of glucose into the upper chamber. Another aliquot was removed from the upper chamber 10 min after cessation of pulse application. In control studies, the SC was pre-pulsed for 10 min with buffer only (no lipid) and then glucose added in the lower chamber and pulsed for three further periods of 10 min each.

Figure 1:
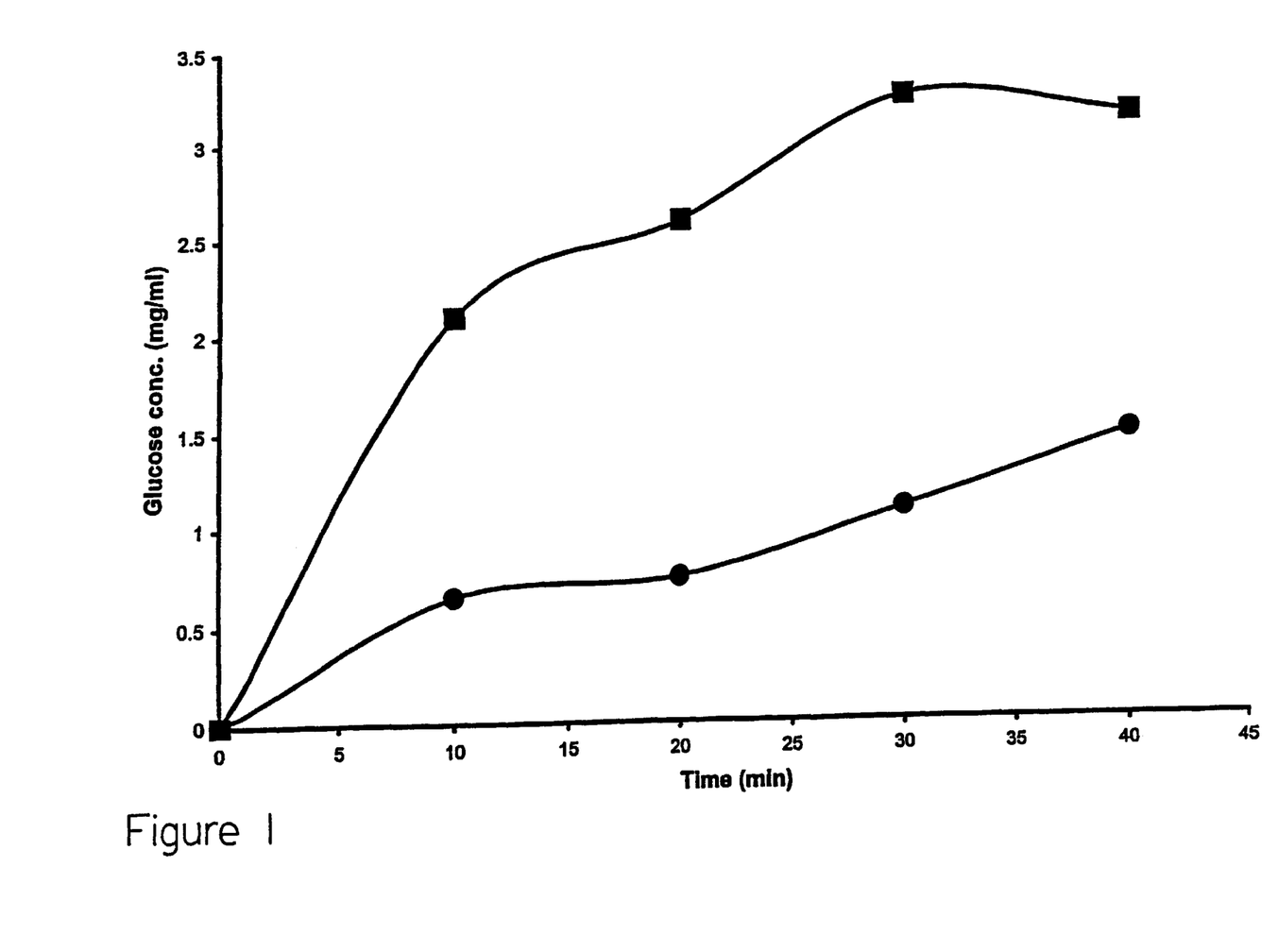
FIG. 1 is a representation of the transport of glucose through porcine SC after eletroporation using negative pulses with 10, 20 and 30 min of pulse application and after an additional 10 min without pulse. The SC was treated with (■) and without (●) DOPG:DOPC liposomes.

The amount of the glucose transported to upper chamber was measured in the aliquots removed at different times. Glucose level was measured using a glucometer. The results are shown in FIG. 1. There is a significant increase the transport of glucose in SC treated with the lipid formulation. The transport of glucose in both the experimental and control measurements are due to diffusion through the SC both during and following pulse application through electropores since glucose is uncharged.

Figure 2:
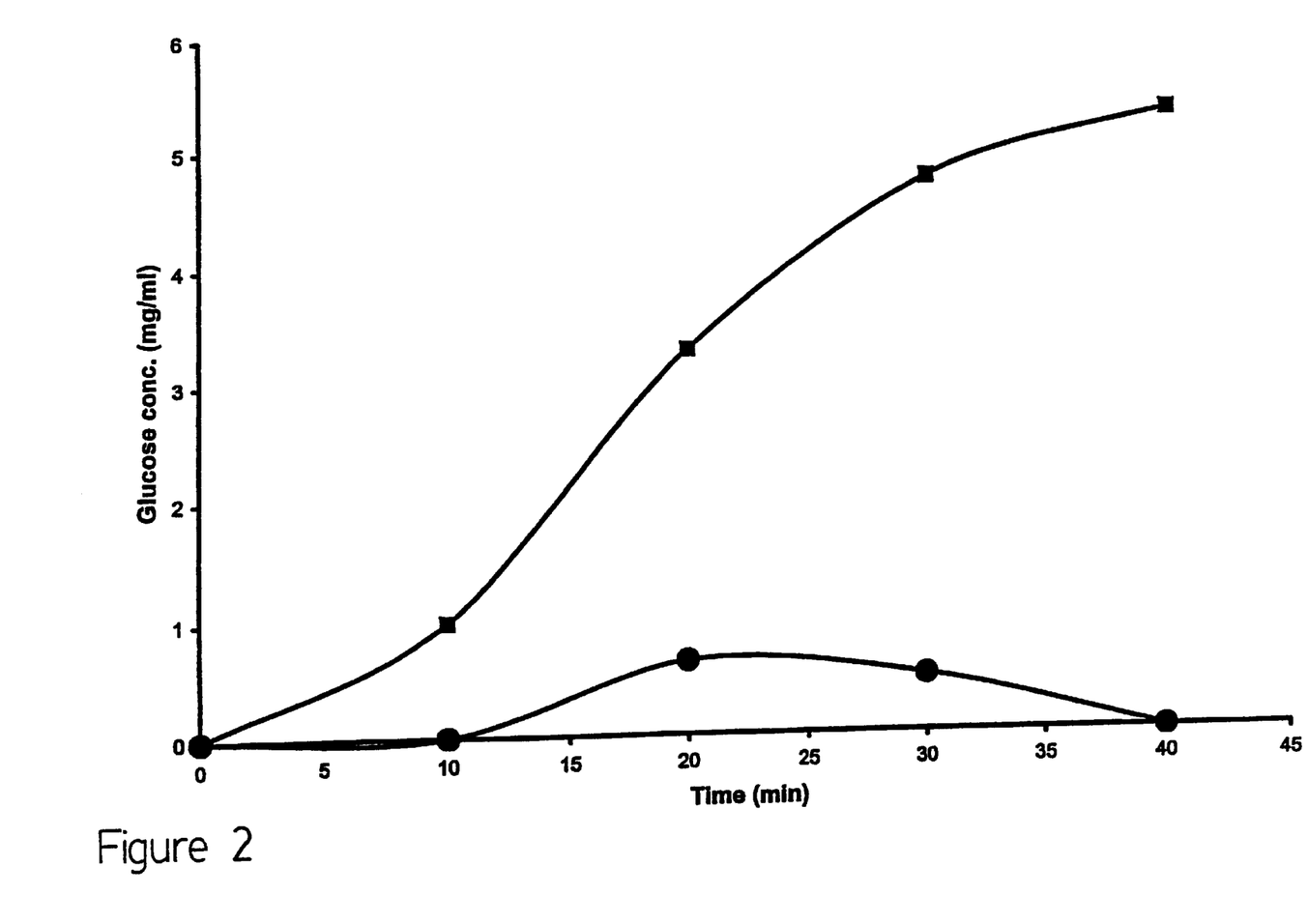
FIG. 2 is a representation of the extraction of glucose through porcine SC. The SC was treated with (■) and without (●) DOPG:DOPC liposomes. Glucose transport was measured after 10, 20 and 30 min of pulse application and after an additional 10 min following the cessation of pulse.

In another illustration of this embodiment, the acceptor side of the SC was treated with the lipid formulation while glucose was added to the donor side of SC. The results are shown in FIG. 2. There is again an increased transport of glucose from the donor to the acceptor chamber when the SC is treated with the lipid as compared to only buffer. Thus, there was a clear enhancement of transport of glucose molecules tested when the SC was treated with the lipid formulation.

EXAMPLE 3

This embodiment illustrates that the presence of liposomes enhances the permeability of whole skin during application of electric pulses. To illustrate this embodiment, freshly excised, full thickness mouse skin was used as a model to investigate the permeability changes following application of varying numbers of electric pulse with and without liposomes. Electrical resistance of the skin was measured as an indicator of skin permeability. The drop in the skin resistance with electric pulse application and the subsequent recovery of the resistance with time after end of pulse application was measured. The time during which the skin resistance remained lower than its base value (before any electric pulse was applied) was taken as the time the skin remained permeable due to electric pulse application.

Electric pulse were applied as described earlier, using a vertical diffusion chamber. The excised full thickness mouse skin was placed between the two aqueous compartments as a barrier. Both compartments were filled with a buffer (10 mM Tris, 100 mM NaCl, 1 mM EDTA pH 8.0). Liposome composition was added to the buffer in the compartment facing the outer surface of the skin for testing the effect of added liposomes. Platinum wire electrodes were placed in the chambers on each side of the skin. Electric pulses were applied using a standard pulse generator (AVTECH, Model AVK-G1-RPCIC1). Electrical resistance was measured by using an AC pulse generator and measuring the voltage drop across the skin and across a known resistance placed in series with the skin.

Figure 3:
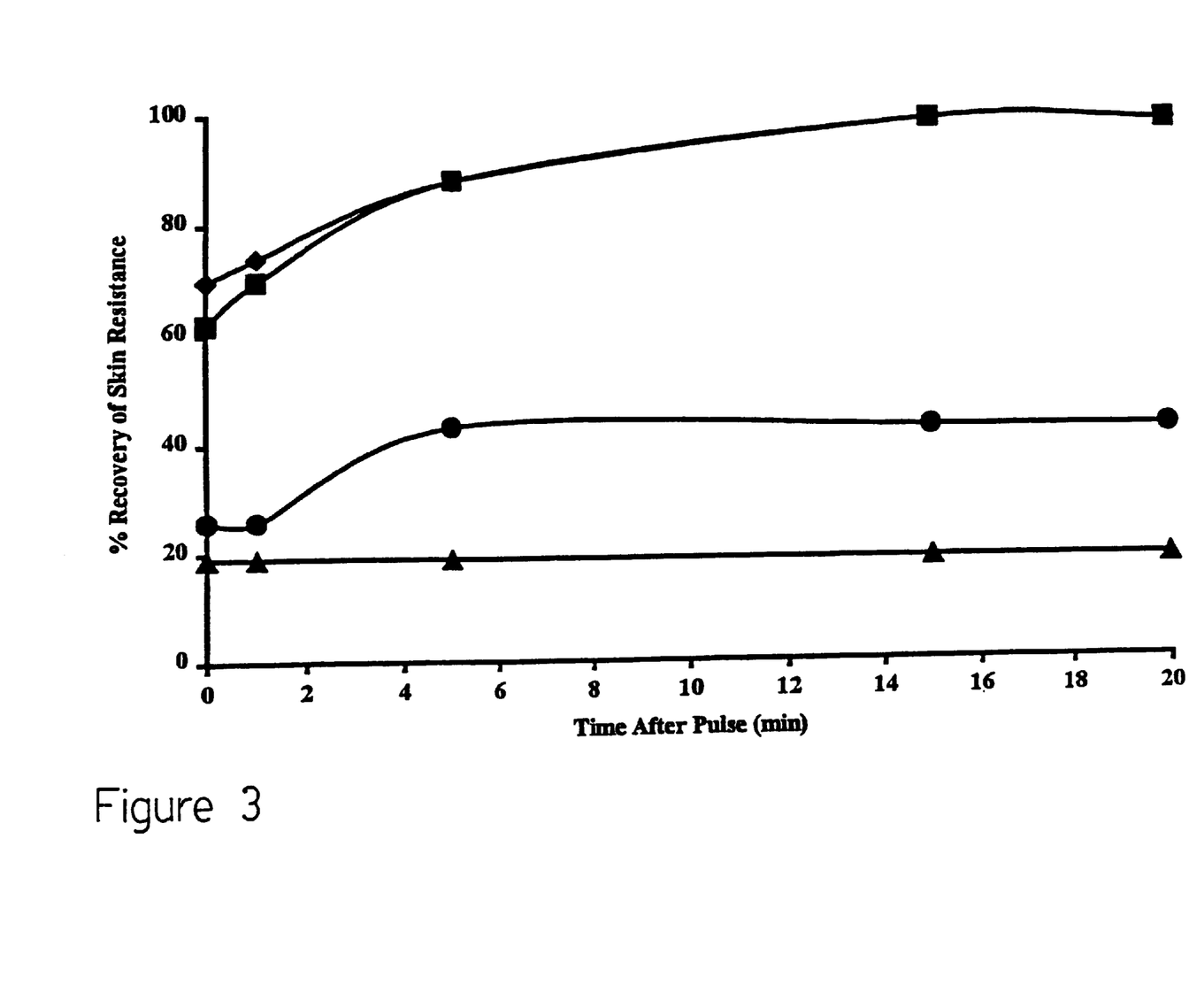
FIG. 3 is a representation of the recovery of electrical resistance of mouse skin following the application of 1 (◆), 2(■), 60 (●) and 180 (▲) pulses of 100V, 1 msec duration.

The results are shown in FIG. 3. The control mouse skin, i.e., without added liposomes, recovered to its base resistance in about 5 minutes after 1 or 2 pulses. There was only partial recovery if the skin was subjected to 60 to 180 pulses. The skin after 60 pulses recovered about 40% of its initial resistance, while after 180 pulses there was no recovery within 20 minutes after pulse application.

Figure 4:
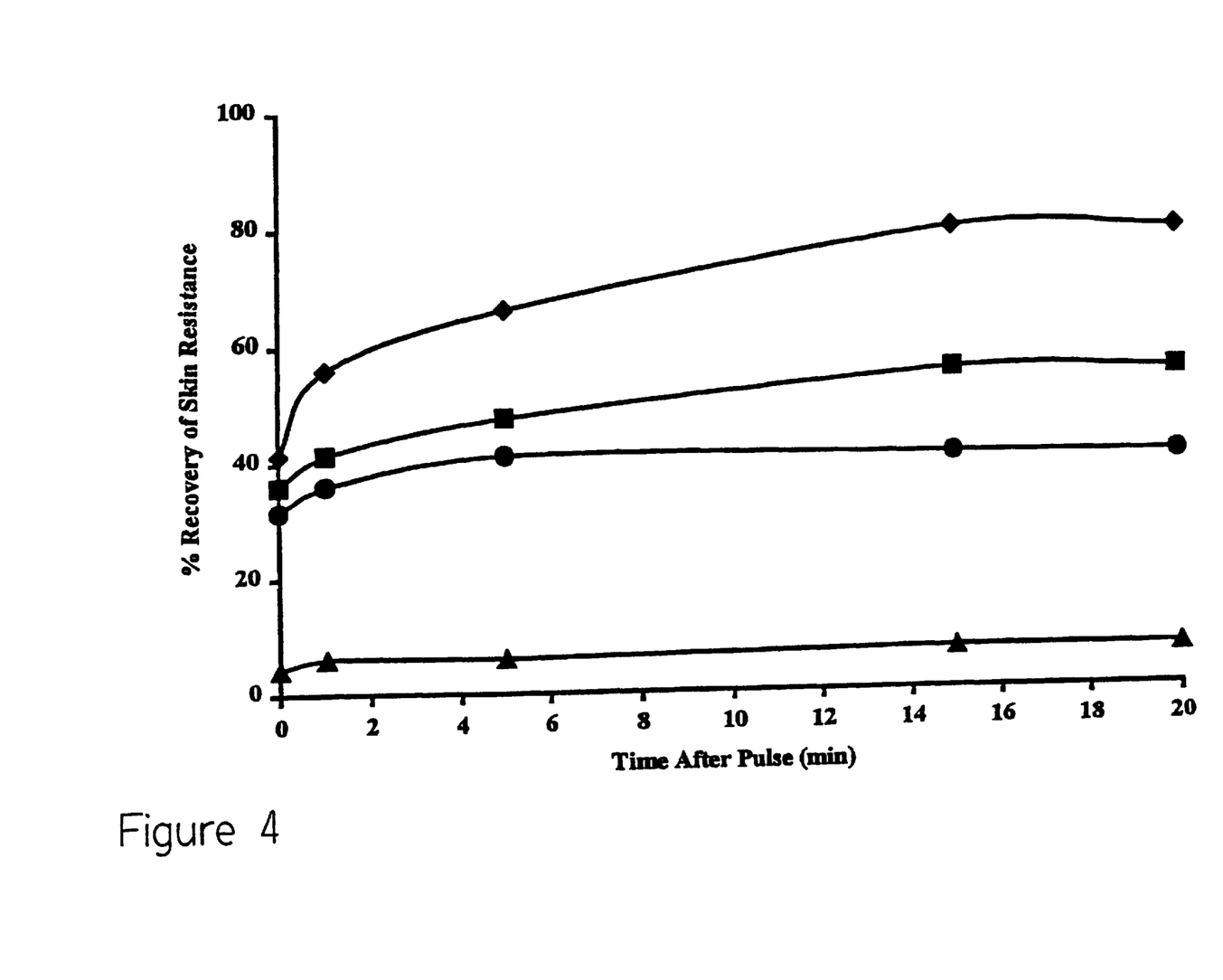

When liposomes were added to the buffer facing the outer skin surface (FIG. 4), the skin did not recover to its initial resistance value even after only one pulse (80% recovery). After 2 pulses the skin recovered to about 50% of its initial resistance. The recovery of resistance after the application of 60 and 180 pulse were similar to that in control (without added liposomes) skin. These results demonstrate that the addition of liposomes reduces the electric resistance during application of electric pulses.

EXAMPLE 4

This embodiment illustrates that the method of the present invention enhances the extraction of glucose in whole animals. Systemic glucose levels in laboratory mice (Strain CD-1, supplier Charles River) were measured by applying electric pulse to bare skin surface on the backs of the animals using a pair of commercially available electrodes. The electrode assembly consists of an Ag/AgCl electrode inside a small reservoir cup (1 cm diameter, 5 mm deep). The cup was filled with cotton wool soaked in buffer alone or buffer with added liposomes. Electrical contact between the electrodes and the skin was established via the buffer-soaked cotton wool. The mice were anesthetized and hair was clipped from backs of the animals to expose bare skin. The mice were kept under anesthesia during the whole procedure. The electrode assemblies were placed on backs of the animals and taped in place. One of the electrodes was maintained at ground potential and negative pulses (~200V, 1 ms pulse duration) was applied to the other electrode using a pulse generator (Velonex, Model 345). This is equivalent to a voltage drop of about 100V across each skin passage. A total of 15 pulses with 1s between each pulse were applied to the electrodes. A third electrode, which was not connected to the pulse generator, was placed close to the other two active electrodes to measure the passive diffusion of glucose through intact skin. After pulse application, the electrodes were removed and replaced with suction cups filled with dry cotton wool and a small vacuum applied to the cups. The suction cups were kept on the skin for 10 minutes after pulse application. The cotton wool from the electrodes, and the suction cups were removed and analyzed for glucose using a glucose assay reagent (Trinder Reagent, Sigma Diagnostics). The glucose measurements were normalized against blood glucose measurements for the individual animals.

The total glucose,extracted through the skin under the negative, ground and passive electrodes and their corresponding suction cup was determined by removing the cotton wool from the electrodes and the suction cups and placing them in the assay reagent. The glucose content was determined spectrophotometrically by comparing the absorbances of the test samples to a standard curve that was obtained using known amounts of glucose.

Figure 5:
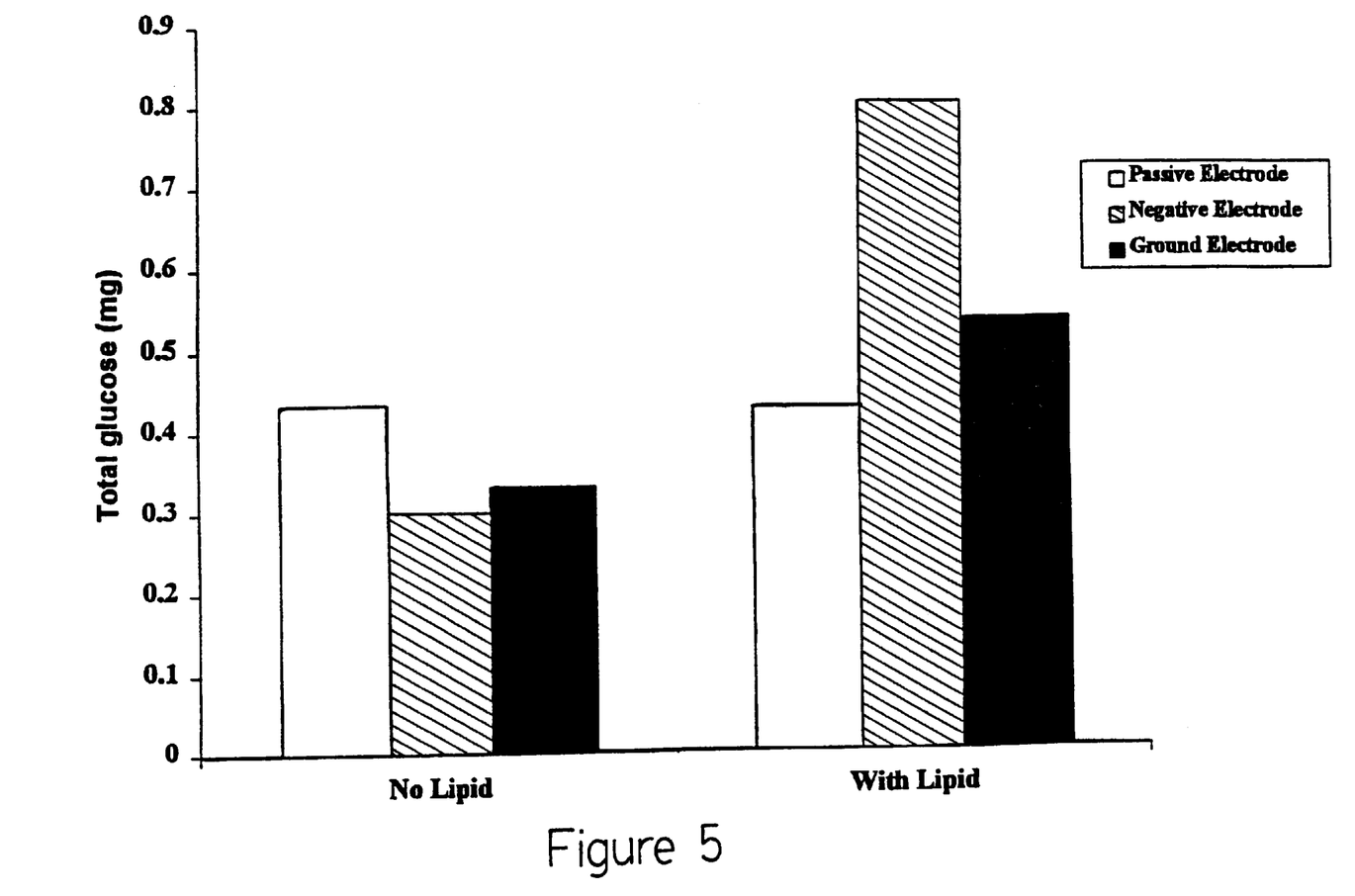
FIG. 5 is a representation of the total glucose extracted through the skin of mice by electroporation by application of 15 pulses of 200V, 1 msec duration.

As shown in FIG. 5, in the absence of added liposomes the amount of glucose extracted through the skin under all three (passive, ground and negative) electrodes were all about the same. When liposomes were added, the extracted glucose under the negative electrode was about twice of that under the passive and the ground electrode. These results demonstrate that the method of the present invention can be used to extract and quantify body analytes.

Figure 6:
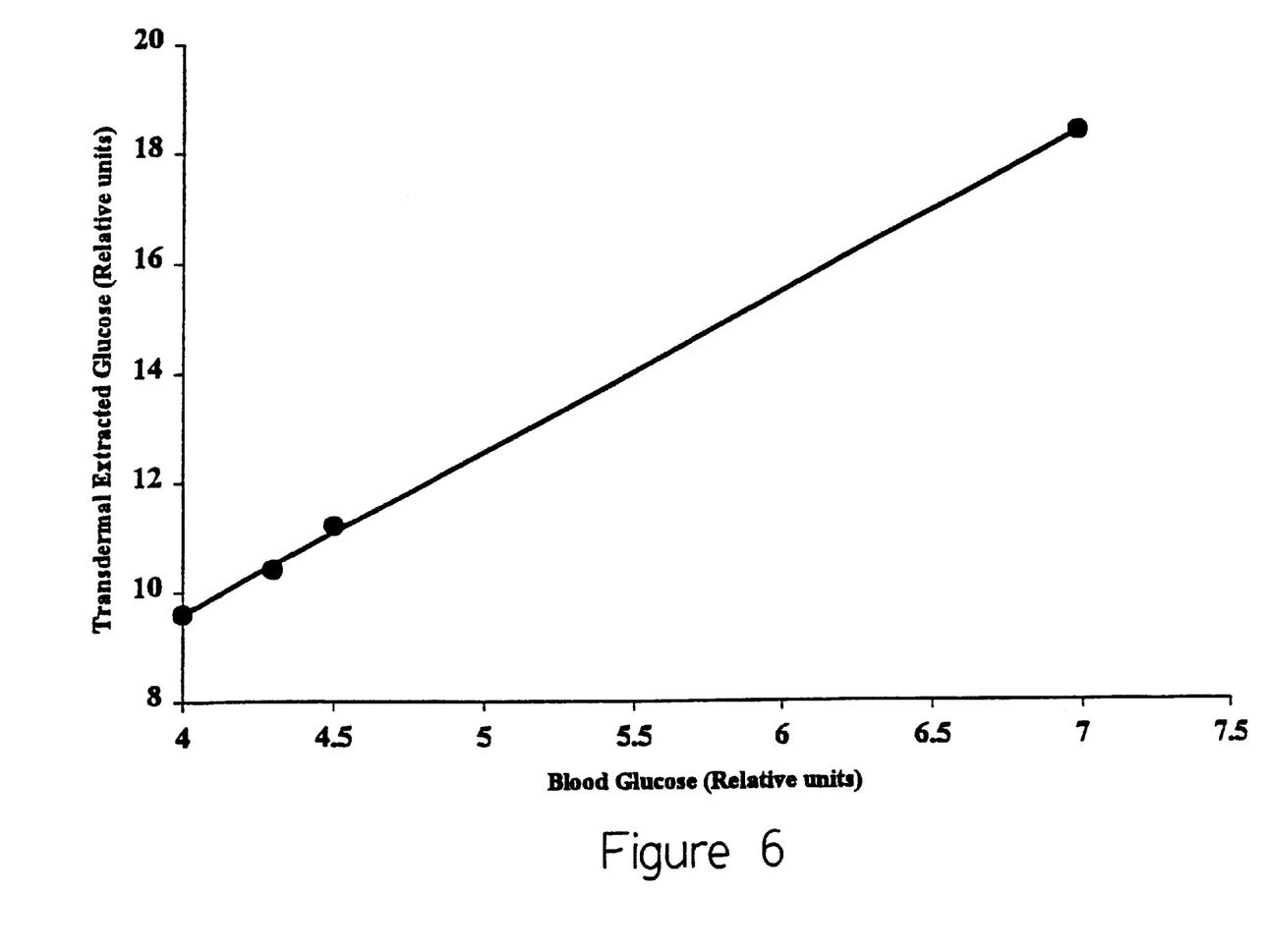
FIG. 6 is a plot of the relationship between extracted glucose and blood glucose. The extracted glucose was measured in the fluid collected at the negative electrode following application of electric pulses in the presence of liposomes.

In another illustration of this embodiment, the relationship between extracted glucose and blood glucose level was determined. Extracted glucose was measured in the fluid obtained at the site of the negative electrode as described above. Blood samples were collected at the same time and blood glucose was determined by a standard method. As shown in FIG. 6, a linear relationship (correlation coefficient of 0.996) was obtained between. the extracted and blood glucose levels. These data demonstrate that the method of the present invention can be used to determine the level of analytes in an individual's body.

The foregoing description of the specific embodiments is for the purpose of illustration and is not to be construed as restrictive. From the teachings of the present invention, those skilled in the art will recognize that the method may be modified without departing from the spirit of the invention.

We claim:

1. A method for measuring an analyte in an individual's body comprising the steps of:
  a. contacting a region of the skin from the individual with a liposomal composition comprising negatively charged lipids;
  b. applying at least one electric pulse to the region of the skin where the liposomal composition has been contacted;
  c. applying suction to said region of the skin where the electric pulse has been applied to extract fluid from the individual;
  d. measuring the analyte in the extracted fluid, and
  e. correlating the analyte level in the extracted fluid to the level of the analyte in the individuals body.

2. The method of claim 1, wherein the liposomal composition comprises dioleylphosphatidylglycerol.

3. The method of claim 2, wherein the liposomal composition further comprises dioleylphosphatidylcholine.

4. The method of claim 3, wherein the dioleylphosphatidylglycerol and the dioleylphosphatidylcholine are present in about a 1:1 ratio.

5. The method of claim 1, wherein the analyte is glucose.

6. The method of claim 1, wherein the electric pulse is applied for a duration of about 10 µsec to about 10 msec and the voltage drop across each skin passage is about 30V to about 180V.

7. A method for measuring an analyte in an individual's body comprising the steps of:
  (a) applying at least one electric pulse in the presence of a liposomal composition to a region of the skin of the individual, wherein the liposomal composition comprises negatively charged lipids;
  (b) applying suction to said region of the skin to extract fluid from the individual;
  (c) measuring the analyte in the extracted fluid; and
  (d) correlating the level of the analyte in the extracted fluid to the level in the individual's body.

8. The method of claim 7, wherein the liposomal composition comprises dioleylphosphatidylglycerol.

9. The method of claim 8, wherein the liposomal composition further comprises dioleylphosphatidylcholine.

10. The method of claim 9, wherein the dioleylphosphatidylglycerol and the dioleylphosphatidylcholine are present in about a 1:1 ratio.

11. The method of claim 7, wherein the analyte is glucose.

12. The method of claim 7, wherein the electric pulse is applied for a duration of about 10 µsec to about 10 msec and the voltage drop across each skin passage is about 30V to about 180V.

13. A method for extracting extracellular fluid through the skin of an individual comprising the steps of:
  (a) placing a negative electrode and appositive electrode on the skin, wherein the negative electrode also contains a reservoir, wherein the reservoir contains a liposomal composition comprising negatively charged lipids;
  (b) applying at least one electric pulse through the electrodes;
  (c) applying suction to the region of the skin where electric pulse has been applied to collect the extracellular fluid.

14. The method of claim 13, wherein the liposomal composition comprises dioleylphosphatidylglycerol.

15. The method of claim 14, wherein the liposomal composition further comprises dioleylphosphatidylcholine.

16. The method of claim 15, wherein the dioleylphosphatidylglycerol and the dioleylphosphatidylcholine are present in about a 1:1 ratio.

17. The method of claim 13, wherein the electric pulse is applied for a duration of about 10 µsec to about 10 msec and the voltage drop across each skin passage is about 30V to about 180V.

18. A method of detecting the presence of an analyte in an individual's body comprising the steps of:
  a. contacting a region of the skin from the individual with a liposomal composition comprising negatively charged lipids;
  b. applying at least one electric pulse to the region of the skin where the liposomal composition has been contacted;
  c. applying suction to said region of the skin where the electric pulse has been applied to extract fluid from the individual;
  d. detecting the presence of the analyte in the extracted fluid,
    wherein the presence of the analyte in the extracted fluid is an indication of the presence of the analyte in the individual's body.

19. The method of claim 18, wherein the liposomal composition comprises dioleylphosphatidylglycerol.

20. The method of claim 19, wherein the liposomomal composition further comprises dioleylphosphatidylcholine.

21. The method of claim 20, wherein the dioleylphosphatidylglycerol and the dioleylphosphatidylcholine are present in about a 1:1 ratio.

22. The method of claim 18, wherein the electric pulse is applied for a duration of about 10 µsec to about 10 msec and the voltage drop across each skin passage is about 30V to about 180V.

* * * * *

UNITED STATES PATENT AND TRADEMARK OFFICE
CERTIFICATE OF CORRECTION

PATENT NO. : 6,383,138 B1
DATED : May 7, 2002
INVENTOR(S) : Sen et al.

It is certified that error appears in the above-identified patent and that said Letters Patent is hereby corrected as shown below:

Column 8,
Line 18, change "appositive" to -- a positive --
Line 57, change "liposomomal" to -- liposomal --

Signed and Sealed this

Twenty-third Day of July, 2002

Attest:

JAMES E. ROGAN
Attesting Officer  Director of the United States Patent and Trademark Office

UNITED STATES PATENT AND TRADEMARK OFFICE
CERTIFICATE OF CORRECTION

PATENT NO. : 6,383,138 B1
DATED : May 7, 2002
INVENTOR(S) : Sen et al.

It is certified that error appears in the above-identified patent and that said Letters Patent is hereby corrected as shown below:

Column 1,
Line 4, please insert the following as the first paragraph:
-- This invention was made with Government support under Grant No. R01 GM55864 awarded by the National Institutes of Health. The Government has certain rights in the invention. --.

Signed and Sealed this

Tenth Day of June, 2003

JAMES E. ROGAN
*Director of the United States Patent and Trademark Office*